United States Patent [19]
Stried et al.

[11] 3,957,582
[45] May 18, 1976

[54] PURIFICATION OF UROKINASE

[75] Inventors: Gene Alan Stried, Zion; Peter George Sesin, Waukegan, both of Ill.

[73] Assignee: Abbott Laboratories, North Chicago, Ill.

[22] Filed: Nov. 20, 1974

[21] Appl. No.: 525,334

[52] U.S. Cl. ............................................. 195/66 B
[51] Int. Cl.² ........................................ C07G 7/026
[58] Field of Search ..................... 195/66 B, 66 R

[56] References Cited
UNITED STATES PATENTS
3,755,083   8/1973   Novak.............................. 195/66 B

*Primary Examiner*—Lionel M. Shapiro
*Attorney, Agent, or Firm*—Paul D. Burgauer; Robert L. Niblack

[57] ABSTRACT

This invention relates to the purification of urokinase and more particularly to a method of obtaining urokinase of high potency free of clot-promoting substances such as thromboplastin by treatment of impure aqueous solutions thereof with a modified, cross-linked dextran gel.

6 Claims, No Drawings

PURIFICATION OF UROKINASE

DETAILED DESCRIPTION OF THE INVENTION

Urokinase is a complex protein which is found in human urine in trace amounts. It is a potent blood clot lysing agent and when injected in amounts far greater than those which exist naturally in urine, it will promote the dissolution of blood clots. Because of its great potential in the treatment of thromboembolic disorders, attempts have been made to isolate and purify urokinase to a potency that is useful and a purity that can directly be used for dissolving human blood clots.

Several methods for the isolation and partial purification of urokinase are known, for instance, those described in U.S. Pat. Nos. 2,983,647 and 3,256,158 which use urokinase from a urine source. More modern techniques use tissue cultures as source for urokinase. In that instance, unfortunately, none of the purification procedures known to date or any combination thereof have proven satisfactory to produce a urokinase that can be used directly as an injectable solution.

One of the previously known methods consists in passing a clear, aqueous urokinase solution through a specified ion exchange column whereby numerous impurities are removed, resulting in a higher concentration of pure urokinase in the eluate. Another method, described in the above-mentioned U.S. Pat. No. 3,256,158 consists in treating a urokinase solution with a partially cross-linked dextran gel. Neither one of these methods produce a urokinase solution that can be directly used medicinally. A combination of these methods is also deficient if the urokinase is propagated from human tissue.

The present invention is therefore particularly designed to produce a urokinase solution of highest purity when used in conjunction with older, known procedures for its purification. More particularly, the present invention is directed to a single step which, when carried out in sequence with previously known purification steps for urokinase, produces a urokinase solution of a purity never before attained in such an easy manner.

According to this invention, urokinase is purified by preparing a clear solution thereof in an aqueous medium of pH 6 - 9 having an ionic strength of 2.0 - 5.0 mmho. placing said solution in contact with swelled beads of a basic anion exchange resin having chemically bound thereto at least 3.0 meq./g. of a tertiary or quaternary amine and having an average bead size of between 40 - 120 microns, allowing for sufficient time for ion exchange to take effect at a temperature of between 0° and the boiling point of the aqueous solution, and separating the liquid phase from said resin having adsorbed thereto a substantial amount of the initially present impurities.

In a general embodiment of the present invention, a urokinase solution prepurified by passing through an appropriate cation exchange column such as Amberlite IRC and the like is treated by the method described herein. If the resulting urokinase solution is then treated according to the procedure of U.S. Pat. No. 3,256,158 using an unmodified dextran gel cross-linked with about 6% epichlorohydrin, the urokinase obtained is of higher purity than ever before obtained except through methods being much more difficult to reproduce, to carry out or to manage on a scale beyond a small laboratory batch. Such a three-step procedure which includes the current new step produces urokinase in a purity immediately useable for medicinal purposes.

In a more specific embodiment, the single step to which the present invention is directed is carried out by adjusting the ionic strength of the urokinase solution to 2.5 - 3.5 mmho., although the general range of 2 - 5 mmho. is acceptable. Below an ionic strength of 2 mmho., the urokinase is not easily soluble and above 5 mmho., the impurities contained in said solution will bind too weakly to the anionic exchange resin, resulting in an incomplete removal thereof. Similarly, at a pH below 6, the urokinase will not properly bind to said resin while at a pH above 9, the urokinase may undergo some unwanted modification as enzymes are generally unstable under highly alkaline conditions.

Concerning the tertiary or quaternary amine bound to the anionic exchange resin, the stated minimum of 3.0 meq. is required to insure sufficient binding capacity for the impurities usually associated with urokinase. A practical upper limit for the amount of amine bound to the exchange resin is 4.0 meq. although higher values are acceptable but not easily attainable. Ordinarily, about one gram of dry weight of the defined anion exchange resin is sufficient to purify 2 - 4 million units of urokinase which ordinarily would be placed in a volume of about 7.5 liters of water properly buffered and containing the above-identified ionic strength. However, it is preferred that about twice the amount of resin is used to assure complete removal of impurities. In the case where the resin contains a higher amount of tertiary or quaternary amine than 4.0 meq., lower amounts thereof are required for the same amount of urokinase. In all instances, about 85 - 95% of the urokinase originally present in the solution are recovered by the singlestep process of the present invention.

In order to demonstrate the present invention, reference is made to the following examples which, however, are not intended to be more than illustrations. All purities given for the various steps in this procedure are shown in CTA units of International Standard at absorption at 280 millimicrons and expressed in dry weight as units/mg. of protein which is easily calculatable from the UV spectrum.

EXAMPLE 1 a. Urokinase, isolated from tissue culture medium and containing approximately 200 CTA units/mg. of urokinase is isolated by absorbing it on Amberlite IRC 50 (a cationic exchange resin) equilibrated in 0.05 molar sodium phosphate buffer at pH 6.25. The urokinase is eluted from the resin with 0.5 molar dibasic sodium phosphate of pH 9.0. The purity of the urokinase obtained in this fashion is increased to about 3500 CTA units/mg.

b. This urokinase is then dialized against a 0.1 molar tris-(hydroxymethyl)aminomethane-acetate buffer of pH 6.0 and mixed with a suspension of a weakly basic dextran gel cross-linked with 5 to 15 percent by weight of vinylbenzene and having chemically bound thereto 3.0 - 4.0 meq./g. of diethylaminoethane and having an average bead size of between 40 and 120 microns (marketed as DEAE-Sephadex A-50 by Pharmacia of Uppsala, Sweden). After agitating this mixture slowly for about 15 minutes, it is filtered. The resulting filtrate has dissolved therein the urokinase in a purity of 22,000 CTA units/mg.

c. This urokinase solution is then passed over a column of Sephadex G-75 (according to the method of U.S. Pat. No. 3,256,158) which is equilibrated in 2% sodium chloride, buffered with 0.22% disodium versenate to a pH of 6.5. The eluted urokinase is now obtained in a purity of 64,000 CTA units/mg.

When in the above procedure, step b) is left out, the obtained urokinase has a purity of only 18,000 CTA units/mg. This purity is insufficient for medicinal use as it does not meet the minimum specification of 35,000 CTA units/mg. established by the Committee on Thrombolytic Agents (CTA).

EXAMPLE 2

While in the above example, DEAE-Sephadex was used (weakly basic anion exchanger), the present example uses a strongly basic anion exchanger. The material used is known under the tradename of QAE-Sephadex A-50; it carries functional groups of diethyl-(2-hydroxypropyl)aminoethyl chloride (marketed by Pharmacia of Uppsala, Sweden).

The beads of QAE-Sephadex A-50 are swelled in distilled water for 24 hours and then equilibrated in 0.05 molar sodium phosphate, 0.05 molar sodium chloride at a pH of 6.0 and packed into a glass column of 0.8 centimeter diameter, 110 centimeters high. A solution of urokinase having a purity of 3000 CTA units/mg. is passed through this column and the eluate obtained is found to contain urokinase at the purity of 21,000 units/mg.

Upon a final column passage according to step c) of Example 1, the urokinase potency increases to above 60,000 units/mg.

EXAMPLE 3

In a repetition of step b) of Example 1 but using a 0.1 molar tris(hydroxymethyl)aminoethane-phosphate buffer at pH 8.0 and operating at 3° – 5° C., the purity of the urokinase solution is increased from 1,900 to 50,000 units/mg.

In a repetition of this example, a urokinase solution containing 1,100 units/mg. is increased to a purity of 37,000 units/mg.

Similarly, a urokinase solution buffered with 0.025 molar sodium phosphate and 0.025 molar sodium chloride at pH 8 increased in purity from 900 to 41,000 units/mg. when operating at 3° – 5° C. Using the same buffer system at pH 6.0 at 0° – 5° and at room temperature, both produced a urokinase of 15,000 units/mg., starting with a material containing 5,500 units/mg. Both of these materials increase in potency to 55,000 units/mg. Upon passage thereof over a Sephadex G-75 column as per Example 1 c).

While the above examples use weakly or strongly basic dextran gels, other polymeric materials routinely used as gel filtration materials can be used with equally good and satisfactory results, i.e., acrylic resins.

This is easily accomplished by allowing the properly buffered urokinase solution of the above-identified ionic strength to contact said resin for at least 15 minutes. Longer residence time is not necessary for the exchange to take place since the impurities will almost instantaneously bind to the anionic exchange resin. As a result, the current method can be used in a batch operation whereby the resin is slurried into the urokinase solution or, equally good or even better results are obtained when the urokinase solution is passed through a column containing the weakly or strongly anionic exchange resin defined above.

We claim:

1. The process of purifying urokinase comprising preparing a clear solution thereof in an aqueous medium of pH 6 – 9 having an ionic strength of 2.0 – 5.0 mmho., placing said solution in contact with swelled beads of an average size between 40 – 120 microns of a basic anion exchange resin having chemically bound thereto at least 3.0 meq./g. of a tertiary or quaternary amine, allowing for sufficient time for ion exchange to take effect at the temperature between 0° C. and the boiling point of the aqueous solution, and separating the liquid phase from said resin having adsorbed thereto substantially all of the initially present impurities.

2. The process of claim 1 wherein said ion exchange takes place at about room temperature.

3. The process of claim 1 wherein said urokinase solution is slurried up with said anionic exchange resin.

4. The process of claim 1 wherein said urokinase solution is passed through a column containing said anionic exchange resin.

5. The process of claim 1 wherein said aqueous solution of urokinase is buffered with tris(hydroxymethyl)aminoethane.

6. The process of claim 1 wherein said ionic strength is between 2.5 and 3.5 mmho.

* * * * *